(12) United States Patent
Schlag et al.

(10) Patent No.: US 6,358,918 B1
(45) Date of Patent: Mar. 19, 2002

(54) PREPARATION COMPRISING THIOL-GROUP-CONTAINING PROTEINS

(75) Inventors: Guenther Schlag; Seth Hallstroem; Harald Gasser, all of Vienna (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/610,111

(22) Filed: Jul. 5, 2000

Related U.S. Application Data (62) Division of application No. 09/008,583, filed on Jan. 16, 1998, now Pat. No. 6,124,255.

(30) Foreign Application Priority Data

Jan. 17, 1997 (AU) .................................................. 68/97

(51) Int. Cl.⁷ ........................ A61K 38/00; A61K 35/14; A01N 37/18; C07K 1/00; C07K 14/00
(52) U.S. Cl. ............................... 514/2; 514/12; 514/21; 530/324; 530/350; 530/362; 530/380; 530/385; 530/395; 530/404
(58) Field of Search ............................... 514/2, 12, 21; 530/350, 324, 362, 380, 385, 395, 404

(56) References Cited

U.S. PATENT DOCUMENTS

| | | | |
|---|---|---|---|
| 4,900,719 A | 2/1990 | Means et al. | ................. 514/18 |
| 6,124,255 A * | 9/2000 | Schlag et al. | ................... 514/2 |

FOREIGN PATENT DOCUMENTS

| | | |
|---|---|---|
| EP | 0131740 | 1/1985 |
| EP | 0159311 | 10/1985 |
| EP | 0247998 | 12/1987 |
| EP | 0506651 | 9/1992 |
| EP | 0637451 | 2/1995 |
| WO | 94/13329 | 6/1994 |
| WO | WO95/07691 | 3/1995 |
| WO | WO96/30006 | 10/1996 |
| WO | WO97/10493 | 3/1997 |

OTHER PUBLICATIONS

DeMaster et al., Biochemistry, 1995, 34:11494–11499.
Ellman, Archives of Biochemistry and Biophysics 82: 70–77 (1959).
Katchalski et al., J. Am. Chem. Soc. 79: 4096–4099 (1957).
Saville, Analyst 83: 670–672 (1958).
Schlag et al., Shock, Sepsis, and Organ Failure—Nitric Oxide, Fourth Wiggers Bernard Conference, 1994, pp. 310–321.
Stamler et al., Proc. Natl. Acad. Sci. USA, 89: 444–448 (1992).
Zhang et al., The Journal of Biological Chemistry, vol. 271, No. 24, Jun. 1996, pp. 14271–14279.

* cited by examiner

*Primary Examiner*—Avis M. Davenport
(74) *Attorney, Agent, or Firm*—Heller Ehrman White & McAuliffe (57) ABSTRACT

There is disclosed a stable, virus-safe, pharmaceutical preparation comprising thiol-group-containing proteins which are heat-treated and processed such that at least 40% of the thiol groups are capable of being nitrosated, a method of preparing such preparations as well as the use of these preparations.

33 Claims, 3 Drawing Sheets

PREPARATION COMPRISING THIOL-GROUP-CONTAINING PROTEINS

This application is a divisional of U.S. Ser. No. 09/008,583, filed Jan. 16, 1998, issued as U.S. Pat. No. 6,124,255, the entirety of which is hereby incorporated by reference.

FIELD OF THE INVENTION

The present invention relates to S-nitroso protein preparations.

BRIEF DESCRIPTION OF THE BACKGROUND ART

NO is a gaseous molecule formed in many mammalian cells and involved in a whole series of physiological and pathological processes. Thus, the endothelium-dependent relaxation of the vascular smooth muscles is due to NO.

The exact mechanism of the action of NO still is largely unknown. It is assumed that physiologic carrier substances play an important role.

As such possible carrier substances, i.a. S-nitrosated proteins are assumed (Stamler et al., PNAS 89 (1992), 444–448). Thus, several thiol group-containing proteins of the most varying nature and function have been nitrosated, such as, e.g. serum albumin, t-PA and kathepsin B (Stamler et.al., Hallstrom et al. (in: Shock, Sepsis, and Organ Failure —Nitric oxide, Fourth Wiggers Bernard Conference (1994), pp. 310–321)).

For this, bovine serum albumin (BSA) nitrosation levels of 85% (gtamler et al.,) or of 90 to 95%, respectively, for human albumin (Hallstrom et al.) have been reported. It has, however, been shown that with the methodology applied in these publications for determining the S nitroso-binding not only to S-nitrosations, but also other nitrosations, such as, e.g., N-nitrosations to tryptophane residues, or C-nitrosations (to tyrosine) can be detected.

In particular, the spectroscopic measurement at 335 nm-and a molar extinction coefficient of 3869 $mol^{-1}\,cm^{-1}$ proved to be non-specific for the S-nitrosothiol binding. In a publication following upon Stamler et al, the same group could prove by reliable detection ≠thods i.a. that in the produced nitrosated BSA-preparations the free SH groups on Cysteine 34 were nitrosated to 37% at the most (Zhang et al., Journal of Biological Chemistry 271 (24), 1996, 14271–14279).

This level also matches the known fact that in preparations of proteins having potentially free thiol groups, only 20 to 35% are, in fact, present in free, reduced SH form. Particularly in protein preparations derived from blood or which are contacted with plasma or plasma derivatives in the course of their preparation procedure, the remaining 65 to 80% are blocked, mostly by mixed S—S bonds with small, thiolcarrying compounds, e.g. free L-cysteine or glutathione, respectively (Katachalski et al., J. Am. Chem. Soc. 79 (1957), 4096–4099, DeMaster et al., Biochemistry 34 (1995), 11494–11499).

As regards the sulphur-containing groupings in the respective proteins, basically it must be differentiated between those present in tightly bonded or associated form, e.g. as intramolecular saturated disulfide bonds and which are decisive for the conformation of the proteins, and those representing the potentially free thiol group(s). The latter are a known parameter for the respective protein. Human serum albumin, e.g., in its native state has a single potentially free thiol group per molecule, i.e. cysteine at position 34. These potentially free thiol groups, however, tend to form intermolecular disulfides, and therefore they are also termed mixed disulfides. In plasma, up to 80%. of these thiol groups are present as mixed disulfides and thus are not directly available as free thiol groups.

In tests, in which a preparation of human serum albumin wherein only 20% of cysteine-34 was present in the reduced, and thus free, form, was treated with dithiothreitol (DTT) prior to nitrosation so as to reduce the mixed disulfides of the potentially free SH group, various nitrosation levels could be attained in dependence on the nitrosation agents and reaction conditions (DeMaster et al.).

There is a problem with the reduction of potentially free thiol groups to free reactive thiol groups, if in addition also the conformation-determining disulfide bonds are broken up and thus the nativity of the proteins is lost. A further problem occurs in proteins or protein solutions which have previously been subjected to a treatment for inactivating possibly present pathogens, e.g. a heat treatment. It is then that i.a. a tendency to increased aggregate formation is observed.

SUMMARY OF THE INVENTION

The present invention aims at providing a protein preparation that is nitrosated or that is capable of being nitrosated, as well as a method of preparing the same, whose thiol groups can be nitrosated to a greater extent and which have an increased S-nitrosation level as compared to preparations already disclosed, for the higher the nitrosation level of the protein preparation, the higher the NO-coupled effect, e.g. when pharmaceutically administering such a protein preparation. In particular, a stable, virus-safe pharmaceutical preparation having a high S-nitrosation level is to be provided.

DESCRIPTION OF THE PREFERRED EMBODIMENTS

According to the invention, the set object is achieved by a preparation comprising thiol-group-containing proteins which are heat-treated, dissolved, and which are characterized in that they are processed. Thus, at least 40% of the thiol groups are capable of being nitrosated.

For, surprisingly it has been found that, in spite of their heat treatment, these virus-inactivated thiol-group-containing protein compositions can be processed such that the potentially free thiol groups are, in fact, available as reactive groups for further reactions. Thus it is possible to enable a high nitrosation level of these proteins even in such virus-inactivated protein compositions, without adversely affecting the nativity of these proteins.

Basically, the pharmaceutical preparation according to the invention may contain any proteins with a "free" thiol group, yet for the purposes of the present invention therapeutically usable proteins are preferred, physiological proteins or human proteins derived from blood, such as albumin, orosomucoid, plasminogen-activator (e.g. tissue-plasminogen activator), fibrinogen, Lys-plasminogen or hemoglobin or also mixtures of such proteins nitrosated or capable of being nitrosated according to the invention, being particularly preferred. According to the present invention, high-molecular proteins are preferred over low-molecular proteins, such as, e.g., glutathione. In particular, the proteins used according to the present invention are those which have a vasodilating and/or anti-aggregating activity on cellular components of the blood. Those proteins which play a decisive role in shock conditions (go-called acute phase proteins) likewise are used according to the invention. In a further preferred embodiment, proteins are used which are suitable as a blood surrogate.

With the method according to the invention, the nitrosation level of the processed thiol group(s) can be varied without any problems, even up to levels corresponding to a complete nitrosation. Yet, since the preparation method according to the invention is the more time-consuming, the higher the nitrosation level is to be, in most cases one has to choose between the nitrosation level and the expenditures of the preparation method, so that preferred preparations are nitrosated to an extent of at least 60%, preferably to an extent of 60 to 95%, in particular 70 to 80%. These levels can be attained by means of the method according to the invention, without higher expenditures.

With the method provided, the preparations according to the invention can be S-nitrosated so specifically that products having a very low N,O,C-nitrosation level of the proteins can be provided. For instance, N-nitroso-compounds are suspected to be cancerogenic, and their delivery kinetics of the NO group is also different from that of S-nitroso-compounds (cf. Zhang et al.), and therefore, in a preferred embodiment of the preparation according to the invention, an N,O,C-nitrosation level of the proteins in the preparation of less than 30, preferably less than 20%, in particular less than 10%, is provided for.

Although it is possible to subject even crude fractions, such as plasma or early plasma fractions or culture liquids, to the processing or nitrosation, respectively, of the invention, the proteins preferably are provided in purified form. The degree of purity should preferably be suitable for a pharmaceutical administration of the proteins. Thus, the preparation according to the invention is prepared on the basis of a purified protein whose degree of purity is at least 80%, in particular at least 90% W/W, based on protein. Higher values are, of course, also preferred. This purified protein may, of course, be formulated to a pharmaceutical preparation with further proteins. Thus, the pharmaceutical preparation according to the invention may be a mixture of various nitrosated proteins, yet it may also be a mixture of a nitrosated and a non-nitrosated protein. Preferably, the pharmaceutical preparation contains human S-nitrosoalbumin and hemoglobin. Preferably, the preparation according to the invention is provided in a purity higher than that of the non-processed or non-nitrosated preparation. Thus, e.g., as a pharmaceutical preparation, human serum albumin frequently is administered in a purity of at least 80% of the total protein. An analogous or higher degree of purity thus is also preferred for the S-nitrosated product. Therefore, nitrosation is followed by an additional purification step.

The pharmaceutical preparation according to the invention preferably is formulated in a pharmaceutically acceptable buffer solution, optionally with pharmaceutically acceptable stabilizers. As a stabilizer, e.g., sodium caprylate and/or sodium acetyl tryptophanate are used. As a rule, it will be possible to use the formulations which are used for the non-nitrosated product. The preparations may be provided as sprays or in a form suitable for topical application. In particular, the preparation is provided in a form suitable for intravenous administration. An i.v. compatible preparation will be particularly characterized by a low aggregate content or will be free from aggregates, respectively. It is, however, also quite possible that the specific use of S-nitrosated proteins is taken into consideration also in the pharmaceutical formulation and that also substances are added which are known to aid the action of S-nitrosated proteins.

Of course, precautions must also be taken for the storage of the preparation according to the invention so that these preparations will remain stable over an extended period of time. For storage purposes, the preparation according to the invention thus preferably is provided in frozen or lyophilized form in which it is storable for a sufficiently long time.

It has been shown that, e.g., for the proteins derived from plasma, in particular for albumin or hemoglobin, the stability in solution will be the longest at a pH of between approximately 6 and 7 in a suitable buffer system (e.g. Ringer's solution).

The pharmaceutical preparation based on a protein having nitrosated thiol groups according to the present invention is stable even after a storage of several days. The stability corresponding to an in vivo half-life could, e.g, also be demonstrated for human albumin which has a half-life of at least 20 minutes, preferably 30 minutes, most preferably at least 40 minutes to 2 hours.

According to a further aspect, the present invention relates to a method of producing a preparation according to the invention, which is characterized by the following steps:

heat treating a composition comprising thiol-group-containing proteins, providing and processing the proteins so that at least 40% of the thiol groups are capable of being nitrosated, and optionally nitrosating the thiol groups of the processed proteins in the composition.

The method according to the invention differs essentially from the methods according to the prior art (Stamler et al., e.g.) in that a specific processing step is provided for the proteins in which the "free" thiol groups are deblocked and thus are capable of being nitrosated.

The processing step must, however, be carried out under conditions in which the conformation stabilizing disulfide bonds are retained as far as possible, since otherwise the latter could also, i.a., be cleaved to thiol groups and could also be nitrosated in the subsequent reaction. The spatial structure of the proteins, as well as the molecular weight are more or less negatively affected thereby. The resultant heterogeneity must, of course, be avoided as far as possible for proteins capable of being pharmaceutically used. For proteins to be used for diagnostic or other purposes, however, a (slight) negative affect on the spatial structure of the proteins is acceptable.

According to the invention, by processing, either the purposeful selection of a protein in which at least 40% of the thiol groups are capable of being nitrosated, or the carrying out of suitable processing measures so that then at least 40% of the thiol groups are capable of being nitrosated is to be understood.

Particularly with starting materials which have already been subjected to a method for inactivating viruses possibly present, particularly to a heat treatment, this processing step may be very critical. For processing may only be effected to that extent in which the potentially free thiol groups are made to be freely accessible, while the conformation-determining disulfide bonds are to remain unchanged.

Such measures may comprise various methods, such as, e.g., incubation in aqueous solution under monitored conditions, incubation with organic substances, such as, e.g., β-propiolactone, incubation in weak acidic medium, enzyme treatment or various separation methods for separating proteins which are only little capable of being nitrosated or which have a low nitrosation level. Thus, also proteins, in which the thiol groups are capable of being nitrosated to an extent of at least 40% are separated from unsuitable proteins which do not meet this criterion. The extent of the capability of being nitrosated may, e.g., be determined by determining the free thiol groups.

Preferably, the processing step according to the invention is carried out by a reductive treatment, and the latter may be effected with known reducing agents, such as, e.g., monothiol group-containing compounds, preferably β-mercaptoethanol. In general, the reducing agent is selected under the assumption that a reaction with the respective protein can be carried out under gentle, non-denaturing conditions. Preferably, the reducing agent has a low toxicity, in particular an agent is selected which is capable of being separated by simple methods after completion of the reaction. Therefore, in a preferred embodiment, an agent such as, e.g.,dithiothreitol (DTT) is not used.

The separation of the reaction agent or of the reaction products, respectively, is effected before or after the nitrosation reaction, and preferably to a quantitative extent or up to a level that is below the detection limit. The respective means used for processing may optionally also be immobilized on a solid carrier material, so that they are particularly simple to remove after the desired reaction has taken place.

In a further preferred embodiment, the preparation according to the invention is characterized by a low content of aggregates. In particular, the portion of aggregates in the pharmaceutical preparation is below 20%, preferably below 10%, most preferred below 5%.

To enable a specific deblocking of the potentially free thiol groups in the processing step, in particular when using a reducing agent, this step preferably is carried out at a temperature of below 20° C., more preferred at temperatures of between 2 and 10° C., and for a period of time of between 1 and 100 hours, more preferred during 12 to 48 hours. It has been shown that such low temperatures have an extremely positive effect on the specificity of the processing step, yet the (complete) deblocking reaction takes accordingly longer at lower temperatures. Although it is possible with a long processing time to attain complete deblocking of the respective thiol groups, it has shown that with a treatment time of between 12 and 48 hours, as a rule 80 to 90% of these thiol groups will be deblocked, and this is considered sufficient for many purposes. In the industrial production of the preparations according to the invention, thus one will always have to balance the nitrosation level to be attained against the duration of the method.

Of decisive importance for the method of the invention is also that the nitrosation step of the processed proteins is carried out under aerobic conditions, in particular if one works with acidic sodium nitrite.

Preferably, the nitrosation according to the invention is carried out with an agent selected from $HNO_2$, HNO, NOCl, $NO^+$, $RNO_2$, $N_2O_3$, $N_2O_4$, $NO_2$— and NO— radical, and in an acidic medium. Also organic NO donors may be used according to the invention.

What is decisive for the extent of the S-nitrosation is in particular the type of nitrosating agent used, and also the ratio of the agent relative to the content of thiol groups of the protein.

To keep the level of N-nitrosation as low as possible, the nitrosation should be carried out only with a relatively low excess of the respective agent, preferably the agent for the nitrosation will be added in a ratio of 0.5:1 to 6:1, preferably at a ratio of 1:1 to 2:1, based on the content of thiol groups of the protein. Also the duration of nitrosation should be as short as possible, since S-nitrosation occurs more rapidly than N-nitrosation. Thus, preferably nitrosation will be carried out for a period of time of from 2 minutes to several hours, preferably 30 minutes, at a temperature of between 15 and 30° C., preferably at room temperature, in an aqueous solution at pH 0.3 to 3.5, most preferred at pH 1.0 to 3.0, preferably in an acidic range up to pH 5, medium.

All types of protein fractions can be used as the starting material for the method according to the invention, i.e. in particular also blood, plasma, serum, a plasma fraction or a purified protein preparation, yet also culture supernatants or respective extracts. If, however, substances are contained in the starting material which may negatively affect the processing or the nitrosating step, such as, e.g., low molecular thiol-group containing proteins, the latter preferably should first be separated. Preferred plasma frations are those according to Cohn fractionation and in particular the Cohn II and III fraction or the Cohn IV fraction.

Within the scope of the method according to the invention also a whole series of further purification steps may be provided at any desired point of the method. Thus, a preferred embodiment of the method according to the invention is characterized in that at least one further purification step, selected from precipitation, gel filtration, diafiltration, ultrafiltration and chromatographic purification, is provided. Albumin, e.g., is purified by means of an ion exchange chromatography.

In particular it may be provided that a purification step is carried out after the processing and/or after the nitrosation, so that the substances used there will neither influence one another nor be present in the finished protein preparation. Preferably, this purification step will be carried out in the form of a chromatographic purification, in particular by means of gel permeation chromatography.

To ensure the virus safety, the preparation of the invention is heat treated, in particular according to EP 0 159 311-A or EP 0 637 451. According to a preferred embodiment, a heat treatment will be carried out at a temperature around 60° C. for a period of time of between one and ten hours. To inactivate or deplete pathogens possibly present, in particular viruses, a series of further physical, chemical or chemical/physical methods may be carried out. Merely by way of example, a hydrolase treatment according to EP 0 247 998-A, a radiation treatment, a nanofiltration or a treatment with organic solvents and/or tensides, e.g. according to EP 0 131 740-A, will be listed here. Further suitable virus inactivating steps in the production of the preparations according to the invention have been described in EP 0 506 651-A or in WO 94/13329-A.

The treatment for inactivating viruses preferably is carried out already before processing is effected, it may, however, also be terminal, i.e. following the nitrosation.

After the nitrosation, the preparation according to the invention may be worked up into a pharmaceutical preparation in a manner known per se. For this, as a rule, the formulation instructions for non-nitrosated protein preparations are followed (cf. pharmacopoeia).

According to a further aspect, the present invention relates to the use of thiol-group containing proteins for the production of a nitrosated pharmaceutical preparation for various medical applications.

Preferred medical applications of this preparation of the invention comprise the production of a preparation for improving the perfusion or micro-circulation, preferably in vital organs, such as, e.g., in the brain (cerebral ischemia), in the heart (myocardial infarct), in the kidneys, in the liver or in the extremities, or in the entire organism, respectively. Thus, the preparation of the invention may generally be used for the prevention or treatment, respectively, of ischemia and reperfusion damage. The preparation according to the invention is also suitable for the treatment of shock, in particular traumatic, hypovolemic and, respectively, hemorrhagic or neurogenic shock. The preparation according to the present invention may be used in different surgical areas, e.g. transplantation surgery and all surgical interventions with subsequent reperfusion. It is especially suitable for the treatment and/or prevention of restenosis following angioplasty.

The preparation may also be used for the treatment and/or prevention of thrombotic conditions, i.e. those involving platelet adhesion/aggregation. In a preferred embodiment S-NO-tissue plasminogen-activator may be used as a thrombolytic agent.

A further purpose of the present preparation is its use in hypertonic crises.

The preparation is further applicable for relaxation of the non-vascular, smooth muscle system, like e.g. airway smooth muscle. Therefore the preparation according to the present invention may be used for the treatment and/or prevention of respirator;y disorders. It may also be useful in diagnosis and/or treatment of male erectile dysfunctions.

The medical preparation is preferably provided in a dose corresponding to maximal that of the non-nitrosated protein.

An advantage of the nitrosated preparation according to the invention also consists in that on account of its high S-nitroso content it can be administered in smaller amounts than preparations having a substantially lower S-nitroso content. What is also important is that the release of the active NO groups of the proteins used according to the invention takes place over a longer period of time, and, on the whole, the kinetics of this reaction is advantageous under physiological conditions.

The amount or dose to be administered will depend on the requirements of the patient, e.g. on parameters such as blood pressure, hematocrite, venous pressure or albumin level, and it may be quite different from case to case. For adults, the recommended dose will, e.g., be from 20 to 40 g per day, for children, e.g., it will be between 0.3 and 0.6 g/kg. As the lower limit, 1 $\mu$mol/kg is recommended. For the platelet aggregation/adhesion inhibiting effect, however, also a lower dose can be used.

The preparations according to the invention may, of course, also be used for any indication of non-nitrosated proteins, since their physiologic effect is maintained despite their nitrosation. In addition, however, conditions requiring the provision of an increased NO content are preferred indications for the preparations according to the invention.

The present invention will now be explained in more detail by way of the examples and drawing figures, to which, however, it shall not be restricted.

EXAMPLE 1

Preparation of an S-nitrosated Human Serum Albumin Preparation without Processing Heat-inactivated human albumin 20% (trade name) of IMMUNO AG, Vienna, was used as the starting material. Nitrosation of the albumin was effected with a 12-fold molar excess of NaNO$_2$ in 0.2 mol/l HCl for a period of 30 minutes at room temperature in the otherwise unchanged medium of the commercial product. Subsequently, it was neutralized with 1 M NaOH. To separate undesired reactants, a preparative gel permeation chromatography was carried out by using a Toyopearl TSK HW 40 (F) gel. Elution was effected with bidistilled water at 4° C. The nitrosated albumin can be lyophilized. The S-nitroso level was determined as described in Example 3 and amounts to 25%.

EXAMPLE 2

Production of an S-nitrosated Human Serum Albumin Preparation after Processing

Heat-inactivated human albumin 20% (trade name) of IMMUNO AG, Vienna, was used as the starting material.

a) Processing:

The starting material was admixed with a 10–20-fold molar excess of β-mercapto ethanol in a phosphate buffer consisting of 50–100 mM sodium phosphate, 0.1–0.2 mM EDTA, 150 mM NaCl, and adjusted to pH 6.0–6.2 with HCl and incubated in a nitrogen atmosphere for a period of between 12 and 48 hours at 4° C. under the exclusion of oxygen. By this, a substantial portion of the mixed, inter-molecular disulfides present in the starting product to an extent of up to 80% could be reduced. The detection of free thiol groups was effected by means of the Ellmann reaction (cf. Example 3).

b) Purification was effected as in Example 1.

c) Nitrosation: Nitrosation of the processed and purified albumin was effected with NaNO$_2$ (1:1 to 1:1.5; freely available thiol groups to NO$_2^-$) in 0.2 mol/l HCl at pH 1.5–2.5 for a period of between 15 and 30 minutes at room temperature. Subsequently, it was neutralized with 1 M NaOH.

d) Purification was effected as in Example 1.

Subsequently, the purified S-nitroso albumin was lyophilized. The S-nitroso level was determined as described in Example 3 and amounts to 63%.

EXAMPLE 3

S-nitroso Level Determination by Means of HPLC by Using the Saville Reaction With Increasing Concentration of Nitrosating Agent The method is based on the principle of separating the protein from excess nitrosating agent and the buffer substances by means of a gel permeation column (Toyopearl TSK HW-40-S). Subsequently, the Saville reaction is carried out by post-column derivatization (Saville B., Analyst Vol. 83, 1958, p.670–672). For this, a selective cleavage of the NO group from RS-NO by Hg$^{2+}$ is effected. Simultaneously, a colour reaction with the nitrite formed is detected at 541 nm.

The chromatograms represent nitrosations of proteins, in particular HSA, with increasing molar concentrations of agent to protein (cf. FIG. 1: a) 0.1; b) 0.5; c) 1; d) 2; e) 6; f) 12 and g) 0). The percentages listed are the actual S-nitrosation levels on the protein, according to the Saville principle. The second peak in the respective chromatogram results from the excess of nitrosation agent, in particular NO$_2^-$.

EXAMPLE 4

Determination of the S-nitrosation Level of a Preparation Described in the Prior Art as Compared to a Preparation According to the Invention An S-nitroso-human albumin preparation was prepared according to Stamler et al. and compared to a preparation prepared according to the invention (cf. Example 2).

There, the S-nitrosation level was first calculated by means of the extinction coefficient $\epsilon=3869$ M$^{-1}$ cm$^{-1}$ at 335 nm for S-nitroso thiols. It was shown that with this determination method, an S-nitroso level of 90% could be determined for the product according to the prior art, as compared to only 25%. for the product according to the invention. According to the method of Stamler, an alleged nitrosation level of 90% determined by means of $\epsilon$ could be attained only with a 12-fold excess of nitrosating agent.

For both products, the ratio of free SH groups per mol protein prior to nitrosation was determined by means of the Ellmann reagent (Ellmann G. L., Arch. Biochem. Biophys. 82, 70, 1958), and it was shown that for the product described in the prior art expected values around 25% were found, whereas for the processed product according to the invention, already 65–80% of the potentially free thiol groups present in the preparation were already free after processing according to Example 2a for 12 hours with β-mercapto ethanol at 4° C.

Finally, the determination of the S-nitroso level by means of HPLC by using the gaville reaotion (cf. Example 3), which proved extremely specific to the S-nitroso binding, showed that in the prior art product only 20–30% of all the potential nitrosation sites were occupied, whereas in the product according to the invention between 60 and 75. of the "free" SH groups are capable of being nitrosated or had been nitrosated, respectively.

A comprehensive illustration of the results can be taken from Table 1.

TABLE 1

| | S—nitroso-level with ε-3869 (mol-S—NO/mol protein in %) un-specific for S—nitrosothiol) | free SH-groups prior to nitro-sation mol SH/mol protein in % (Ellmann-reagent) | S-nitroso-level (mol S—NO/mol) protein in %) HPLC (+Saville-reaction) (specific for S—nitroso thiol) |
|---|---|---|---|
| Prior art | 90% | 25–30% | 20–30%– |
| preparation of invention | 25% | 65–95% | 60–90% |

EXAMPLE 5

Comparison of the Nitroso Level Determination (according to Stamler et al.) with the HPLC/Saville Reaction Determination, With Varying Excess of Nitrosating Agent A human serum albumin preparation was nitrosated according to the invention and following Example 2, with an 0.5, 1, 2, 6 and 12-fold molar excess, and subsequently the S-nitroso level was measured both by means of the method according to Stamler et al. (with $\epsilon=3869$ M$^{-1}$ cm$^{-1}$ at $\lambda=335$ nm), and the S-nitroso level was proven parallel thereto by means of the HPLC/Saville reaction.

It was shown that by means of the spectroscopical determination method according to Stamler et al., different S-nitroso levels (20%., 39%, 69% and 111%) of the preparations could be determined for each of the 1, 2, 6 and 12-fold excess, whereas the value of Snitrosation level determined by means of HPLC was between 60 and 65% in all the reactions.

Figure 1:
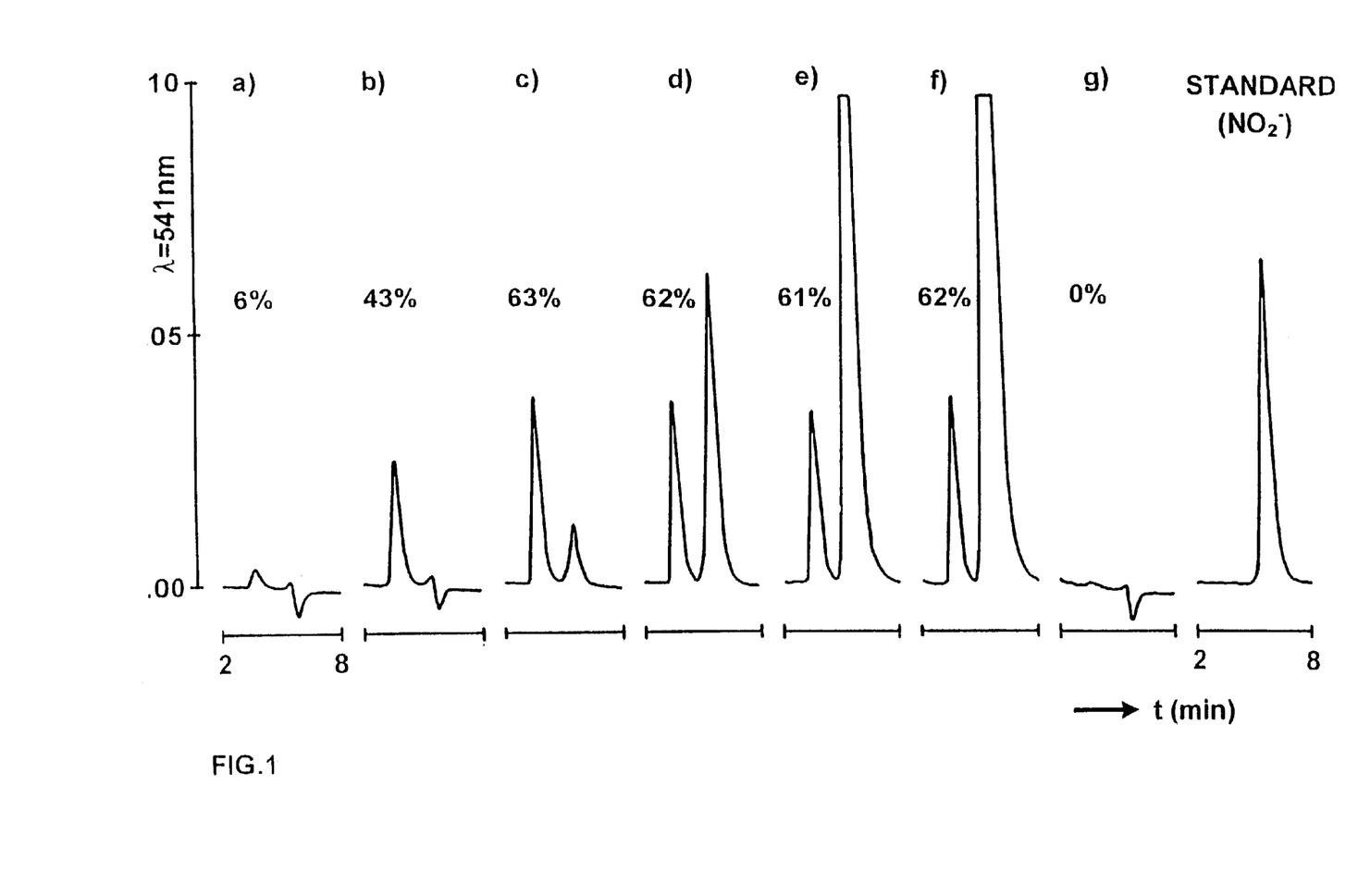
FIG. 1 shows the S-nitroso level determination by means of the HPLC/Saville reaction.
Figure 2:
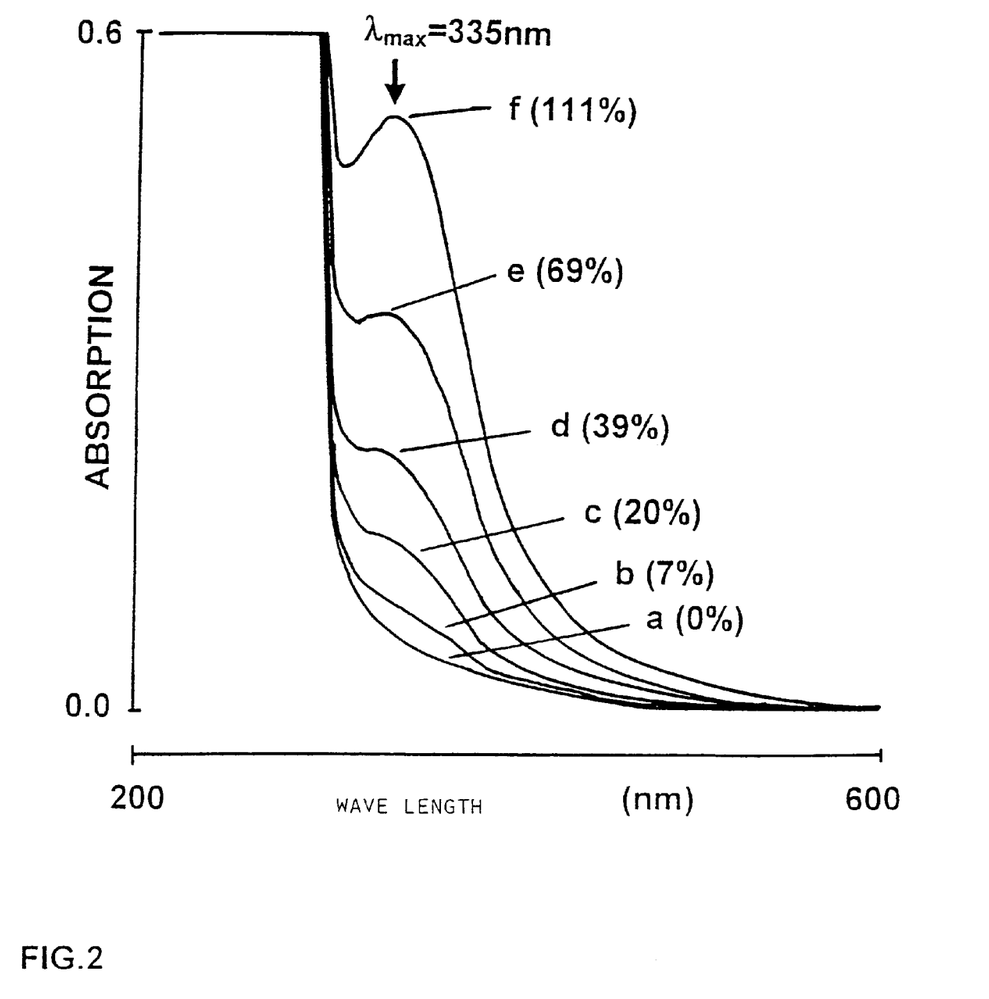
FIG. 2 shows the S-nitroso level determination with $\epsilon=3869$ M$^{-1}$cm$^{-1}$ at $\lambda=335$ nm.

The results are summarized in Table 2 and illustrated in FIGS. 1 and 2.

TABLE 2

| | 0.5 | 1 | 2 | 6 | 12 |
|---|---|---|---|---|---|
| Spectroscopy | 7.2 | 20% | 39% | 69% | 111% |
| HPLC/Saville-Reaction | 43% | 63% | 62% | 61% | 63% |

These results show that the methodology for determining the S-nitroso level as used in the prior art according to Stamler et al. and Hallstrbm et al. is not suitable. Consequently, the levels of S-nitrosation given there are not 85 or 90–95%, but are merely in a range of between 25 and 37%.

Figure 3:
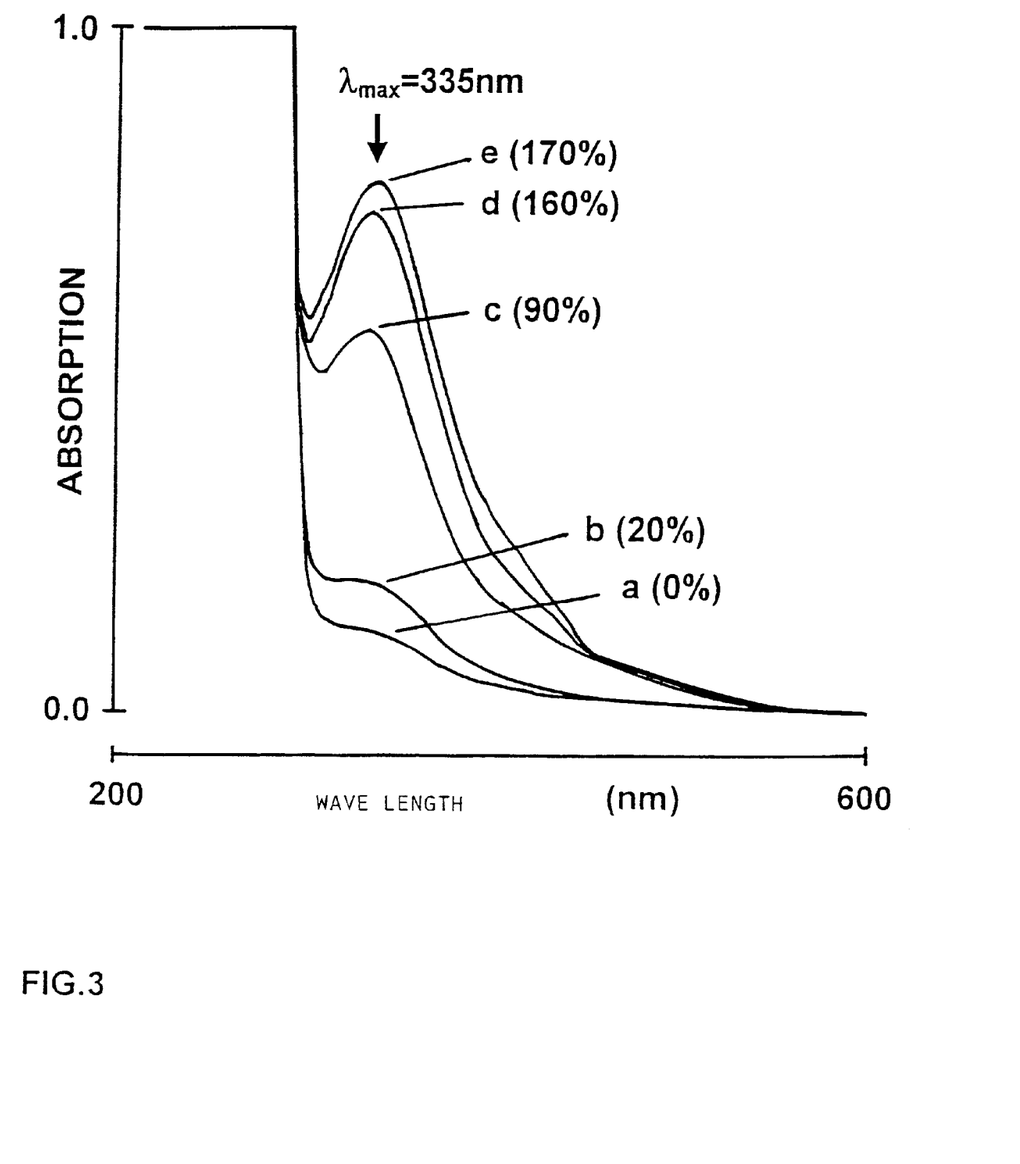
FIG. 3 shows the S-nitroso level determination of S-blocked albumin.

In comparison thereto, the spectrophotometrical determination of the nitrosation level of a modified human serum albumin, in which the free thiol group (Cys 34) has been chemically blocked by carboxy methylation, is illustrated in FIG. 3. Nitrosation was effected in increasing molar concentrations of nitrosating agent to protein (a) 0; b) 1; c) 6; d) 12 and e) 20).

No S-nitrosation could be detected by means of the HFLC poet-column derivatising method (S-nitrosation level<1%).

What is claimed is:

1. A method for improving the perfusion and microcirculation in patients, comprising administering to said patients an effective dose of a stable, virus-safe pharmaceutical preparation comprising thiol-group-containing proteins, said thiol-group-containing proteins being heat-treated and processed such that at least 60% of said thiol groups are nitrosated, and said proteins being selected from the group consisting of albumin, orosomucoid, tissue-plasminogen activator, fibrinogen, Lys-plasminogen, hemoglobin and a mixture thereof.

2. A method as set forth in claim 1 wherein said improved perfusion and microcirculation are the perfusion and microcirculation of the brain, the heart, the kidneys, the liver and the extremities.

3. A method of treating patients suffering from one of cerebral ischemia and myocardial infarct comprising administering to said patients an effective dose of.a stable, virus-safe pharmaceutical preparation comprising thiol-group-containing proteins, said thiol-group-containing proteins being heat-treated and processed such that at least 60% of said thiol groups are nitrosated, and said proteins being selected from the group consisting of albumin, orosomucoid, tissueplasminogen activator, fibrinogen, Lys-plasminogen, hemoglobin and a mixture thereof.

4. A method of treating patients suffering from shock, comprising administering to said patients an effective dose of a stable, virus-safe pharmaceutical. preparation comprising thiol-group-containing proteins, said thiol-group-containing proteins being heat-treated and processed such that at least 60% of said thiol groups are nitrosated, and said proteins being selected from the group consisting of albumin, orosomucoid, tissue-plasminogen activator, fibrinogen, Lys-plasminogen hemoglobin and a mixture thereof.

5. A method as set forth in claim 4, wherein said shock is a traumatic shock.

6. A method as set forth in claim 1, wherein said preparation is adiministered in a dose corresponding to maximal that of non-nitrosated protein.

7. A method of improving perfusion and microcirculation in a patient comprising, administering to the patient a pharmaceutical composition comprising at least one thiol-group-containing protein, wherein the thiol-group-containing protein has been heat-treated and processed such that at least 40% of said thiol groups on said thiol-group-containing proteins are capable of being nitrosated.

8. The method of claim 7, wherein the thiol-group-containing protein is at least one selected from the group consisting of albumin, orosomucoid, tissue-plasminogen activator, fibrinogen, Lys-plasminogen, and hemoglobin.

9. The method of claim 7, wherein at least 60% of the thiol groups of the thiol-group-containing proteins are nitrosated.

10. The method of claim 9, wherein at least 65%–95% of the thiol groups of the thiol-group-containing proteins are nitrosated.

11. The method of claim 9, wherein at least 70%–90% of the thiol groups of the thiol-group-containing proteins are nitrosated.

12. The method of claim 7, wherein the thiol-group-containing protein is at least one selected from the group consisting of human S-nitroso-albumin and hemoglobin.

13. The method of claim 7 herein the thiol-group-containing proteins have an N,O,C-nitrosation level that is less than 30%.

14. The method of claim 7, wherein the thiol-group-containing proteins have an N,O,C-nitrosation level that is less than 20%.

15. The method of claim 7, wherein the thiol-group-containing proteins have an N,O,C-nitrosation level that is less than 10%.

16. A method of treating a patient suffering from at least one of cerebral ischemia and myocardial infarct comprising, administering to the patient a pharmaceutical composition comprising at least one thiol-group-containing protein, wherein the thiol-group-containing protein has been heat-treated and processed such that at least 40% of said thiol groups on said thiol-group-containing proteins are capable of being nitrosated.

17. The method of claim 16, wherein the thiol-group-containing protein is at least one selected from the group consisting of albumin, orosomucoid, tissue-plasminogen activator, fibrinogen, Lys-plasminogen, and hemoglobin.

18. The method of claim 16, wherein at least 60% of the thiol groups of the thiol-group-containing proteins are nitrosated.

19. The method of claim 18, wherein at least 65%–95% of the thiol groups of the thiol-group-containing proteins are nitrosated.

20. The method of claim 18, wherein at least 70%–90% of the thiol groups of the thiol-group-containing proteins are nitrosated.

21. The method of claim 16, wherein the thiol-group-containing protein is at least one selected from the group consisting of human S-nitroso-albumin and hemoglobin.

22. The method of claim 16, wherein the thiol-group-containing protein have an N,O,C-nitrosation level that is less than 30%.

23. The method of claim 16, herin the thiol-group-containing protein have an N,O,C-nitrosation level that is less than 20%.

24. The method of claim 16, wherein the thiol-group-containing protein have an N,O,C-nitrosation level that is less than 10%.

25. A method of treating a patient suffering from shock comprising, administering to the patient a pharmaceutical composition comprising at least one thiol-group-containing protein, wherein the thiol-group-containing protein has been heat-treated and processed such that at least 40% of said thiol groups on said thiol-group-containing proteins are capable of being nitrosated.

26. The method of claim 25, wherein the thiol-group-containing protein is at least one selected from the group consisting of albumin, orosomucoid, tissue-plasminogen activator, fibrinogen, Lys-plasminogen, and hemoglobin.

27. The method of claim 25, wherein at least 60% of the thiol groups of the thiol-group-containing proteins are nitrosated.

28. The method of claim 27, wherein at least 65%–95% of the thiol groups of the thiol-group-containing proteins are nitrosated.

29. The method of claim 27 wherein at least 70%–90% of the thiol groups of the thiol-group-containing proteins are nitrosated.

30. The method of claim herein the thiol-group-containing protein is at least one selected from the group consisting of human S-nitroso-albumin and hemoglobin.

31. The method of claim 25, wherein the thiol-group-containing proteins have an N,O,C-nitrosation level that is less than 30%.

32. The method of claim 25, wherein the thiol-group-containing proteins have an N,O,C-nitrosation level that is less than 20%.

33. The method of claim 25, wherein the thiol-group-containing proteins have an N,O,C-nitrosation level that is less than 10%.

* * * * *

UNITED STATES PATENT AND TRADEMARK OFFICE
CERTIFICATE OF CORRECTION

PATENT NO.     : 6,358,918 B1
DATED          : March 19, 2002
INVENTOR(S)    : Guenther Schlag et al.

It is certified that error appears in the above-identified patent and that said Letters Patent is hereby corrected as shown below:

<u>Title page,</u>
Item [30], Foreign Application Priority Data", please change "(AU)" to -- (AT) --

Signed and Sealed this

Fourth Day of June, 2002

Attest:

JAMES E. ROGAN
*Attesting Officer*          *Director of the United States Patent and Trademark Office*